United States Patent [19]

Watkins et al.

[11] Patent Number: 4,783,444

[45] Date of Patent: Nov. 8, 1988

[54] ANTIGLAUCOMA COMPOSITIONS AND METHODS

[75] Inventors: Robert Watkins, Great Meadows; Ronald J. Doll, Maplewood; Bernard R. Neustadt, West Orange; Elizabeth M. Smith; Charles V. Magatti, both of Verona; Elijah H. Gold, West Orange, all of N.J.

[73] Assignee: Schering Corporation, Kenilworth, N.J.

[21] Appl. No.: 849,072

[22] Filed: Apr. 4, 1986

Related U.S. Application Data

[63] Continuation-in-part of Ser. No. 651,378, Sep. 17, 1984, which is a continuation of Ser. No. 500,494, Jun. 2, 1983, abandoned.

[51] Int. Cl.$^4$ ............................................. A61K 37/02
[52] U.S. Cl. .................................. 514/19; 514/912; 514/913; 514/914
[58] Field of Search .................. 514/19, 912, 913, 914

[56] References Cited

U.S. PATENT DOCUMENTS

| 4,374,829 | 2/1983 | Harris et al. | 514/21 |
| 4,584,285 | 4/1986 | Doll et al. | 514/19 |
| 4,616,012 | 10/1986 | Neustadt | 514/222 |

FOREIGN PATENT DOCUMENTS

| 0050800 | 5/1982 | European Pat. Off. |
| 3410732 | 9/1985 | Fed. Rep. of Germany |

OTHER PUBLICATIONS

Ionitescu, *Rev. Chir* [*Oftalmol*], 26(2), 137–138 (1982).

Primary Examiner—J. R. Brown
Assistant Examiner—F. T. Moezie
Attorney, Agent, or Firm—Joseph T. Majka; Stephen I. Miller; James R. Nelson

[57] ABSTRACT

The present invention relates to ophthalmological pharmaceutical compositions comprising (benzothiadiazine, benzamide and benzenesulfonyl)phenyl-substituted carboxyalkyl dipeptide compounds and to methods for using said composition in reducing intraocular pressure, e.g., in the treatment of glaucoma.

41 Claims, No Drawings

ANTIGLAUCOMA COMPOSITIONS AND METHODS

CROSS REFERENCE TO RELATED APPLICATION

This application is a continuation-in-part of pending application Ser. No. 651,378, filed Sept. 17, 1984, which is a continuation of Ser. No. 500,494, filed June 2, 1983, which is now abandoned.

BACKGROUND OF THE INVENTION

Glaucoma is an ocular disease complex associated with an elevated pressure within the eye (i.e., intraocular pressure, IOP). As a result of the elevated IOP, damage to the optic nerve resulting in irreversible loss of visual function may ensue. Untreated, this condition may eventually lead to blindness.

Ocular hypertension, i.e., the condition of elevated intraocular pressure without optic nerve damage or characteristic glaucomatous visual field loss, is now believed by the majority of ophthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral artereosclerosis due to the possibility of systemic action.

Timolol, a clinically utilized, topically applied agent for lowering intraocular pressure, must be used with caution in patients in whom beta-adrenergic blockade may be undesirable. Systemic absorption of topically administered timolol and systemic beta-blockade are responsible for the contraindication of timolol therapy for glaucoma in patients with compromised pulmonary function and in patients who cannot tolerate its systemic cardiovascular action.

Pilocarpine, a topical drug, although considered systemically harmless and quite effective, may cause considerable local difficulties. Pupillary constriction causes the eye to lose its ability to adapt from light to dark. Accommodation may become stimulated so that the patient's refraction is sometimes incorrect and vision becomes blurred. The drug itself may cause a local vasodilation and red eyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and general malaise. European patent application No. 81400326.5, Publication number 36,351 attempts to overcome these difficulties by the topical administration of an alkali metal salt of a carbonic anhydrase inhibitor.

The present invention provides a new composition and method for reducing and controlling elevated intraocular pressure, especially the elevated IOP associated with glaucoma.

SUMMARY OF THE INVENTION

The invention sought to be patented in its pharmaceutical composition aspect is a topical ophthalmologically acceptable composition useful for reducing and controlling elevated intraocular pressure, especially elevated IOP associated with glaucoma, comprising a compound of formula I $$Z-\text{Ph}-Y-(CH_2)_m-\underset{R^2}{\underset{|}{C}}(\overset{R^1}{\overset{|}{C=O}})-NH-\underset{R^2}{\underset{|}{CH}}-\underset{}{\overset{R^3}{\underset{|}{C}}}-W-COR^4 \quad \text{I}$$

in combination with an ophthalmologically acceptable carrier for topical use, wherein W is $$-N\underset{}{\overset{}{\diagdown}}\underset{R^5}{\overset{}{C-}} , \quad -N\underset{}{\overset{(CH_2)_p}{\diagdown}}\underset{R^5}{\overset{(CH_2)_q}{C-}} ,$$

II    III $$-N\underset{(CH_2)_p}{\overset{}{\diagdown}}\underset{R^5}{\overset{(CH_2)_q}{C-}} , \text{ or } -N\underset{(CH_2)_p}{\overset{[\text{CH}_2]_n}{\diagdown}}\underset{R^5}{\overset{S \times S}{\underset{(CH_2)_q}{C-}}} ;$$

IV    V n is 0 or 1; m is 0 to 2 p and q are each 0, 1 or 2, provided that the sum of p and q is 1 or 2, and that in formula V, p is not 0;

Y is $-CH_2-$, $-CH_2O-$, or $-CH_2S-$, attached at the 2 or 4 position of the phenyl group;

Z is $$R^6HNO_2S-\text{Ph}(A)-\underset{SO_2}{\overset{H\\N}{\diagdown}}\underset{NR^7}{\overset{}{\diagup}}D- , \text{ or}$$

VI $$R^6HNO_2S-\text{Ph}(Cl)-G-$$

VII wherein
A is Cl or CF$_3$;
D is $-(CH_2)_u-$, $-CH_2O-$, $-CH_2S-$;

$$-CH_2\overset{O}{\overset{\|}{C}}NH-;$$

G is $-CONR^7(CH_2)_t-$, or $-SO_2NR^7(CH_2)_t-$; t is 0 or 1;

$R^1$ and $R_4$ are independently hydroxy, alkoxy having from 1 to 8 carbon atoms, $K-X_r-(CH_2)_s-O-$, wherein K is phenyl, substituted phenyl, 1- or 2-naphthyl, X is oxygen or sulfur, r is 0 or 1 and s is 0 or 4, provided that when r is 0, s is 0 and wherein the substitutents on the phenyl are chosen from group M, wherein M is halogen, hydroxy, trifluoromethyl, alkoxy having from 1 to 6 carbon atoms, alkyl from 1 to 6 carbon atoms, 2- and 3-furanyl, 2- and 3-thienyl and phenyl (which phenyl group may be substituted with halogen, hydroxy, trifluoromethyl, alkoxy having from 1 to 6 carbon atoms or alkyl having from 1 to 6 carbon atoms), $-OCH_2-OCO-$alkyl wherein the alkyl has from 3 to 8 carbon atoms, $-OCH_2CO-$ phenyl, wherein the phenyl may be substituted with group M, 1-glyceryl,

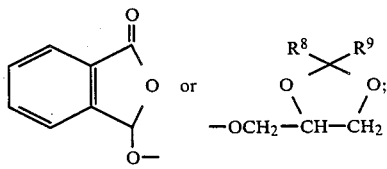

$R^2$, $R^5$, $R^6$ and $R^9$ are hydrogen or lower alkyl;
$R^3$ is hydrogen, lower alkyl or amino lower alkyl;
$R^7$ is hydrogen, lower alkyl or phenyl(lower)alkyl;
$R^8$ is hydrogen, lower alkyl, phenyl, or phenyl substituted by group M;
u is 1 or 2; or a pharmaceutically acceptable salt thereof.

The invention sought to be patented in its pharmaceutical method aspect is a method for reducing and controlling the elevated introcular pressure, especially elevated IOP associated with glaucoma or that resulting from use of steroidal anti-inflammatory drugs in a mammal, e.g., a human, which method comprises administering to said mammal an effective amount of the above-defined pharmaceutical composition.

The invention in another aspect involves two kits for use in reducing and controlling elevated intraocular pressure. Both kits comprise first and second containers, in a single package, wherein in both cases the first container includes a topical pharmaceutical composition comprising an IOP reducing effective amount of a compound of formula I. In a first kit, the second container includes a pharmaceutical composition comprising an anti-inflammatory effective amount of a steroid in a pharmaceutically acceptable carrier. In the second kit, the second container includes a pharmaceutical composition comprising an introcular pressure reducing amount of a beta adrenergic blocking agent in a topical opthamological carrier.

DETAILED DESCRIPTION

The compounds employed in the method and composition of the present invention are the subject matter of Ser. No. 651,378, filed Sept. 17, 1984, the disclosure of which is incorporated herein by reference.

Preferred compounds for use in the invention are those wherein W is represented by formula III, IV or V. When W is of formula III or IV, preferred values for p and q are 0 and 1, respectively; when W is of formula V, preferred values of p, q and n are 1, 1 and 0 respectively.

Two additional groups of preferred compounds are that wherein $R^2$ and $R^5$ are hydrogen, and that wherein $R^4$ is hydroxy.

Particularly preferred compounds are those wherein W is represented by formula III or V; n, p, q, Y, $R^2$, and $R^5$ are as defined above for preferred compounds; $R^3$ is methyl or amino butyl; Z is of formula VI, wherein A is chlorine, or Z is of formula VII and G is $-CON-H-CH_2-$ or $-SO_2NH-CH_2-$; $R^6$ and $R^7$ are hydrogen or methyl; and $R^1$ is hydroxy, ethoxy, methoxy, phenoxyethoxy, or pivaloyloxymethoxy.

As used herein, "lower alkyl" means straight or branched chain hydrocarbon radicals of from 1 to 6 carbons, e.g. methyl, ethyl, propyl, ispropyl, butyl, t-butyl, pentyl and hexyl. Similarly, "lower alkoxy" means straight or branched alkoxy radicals having 1 to 6 carbon atoms, e.g. methoxy, ethoxy, propoxy, butoxy, iso-butoxy, pentoxy and hexyloxy. "Halogen" means fluorine, chlorine and bromine.

Compounds employed in the present invention include various stereoisomers. Preferred stereoisomers are those in which the absolute configuration at each of the three carbon atoms adjacent to both a nitrogen and a carbonyl group corresponds most closely to the absolute configuration of L-amino acids.

The compounds used in this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo or by exchanging the cations of an existing salt for another cation on a suitable ion exchange resin.

Compounds of formula I may be prepared by several routes using methods known in the art.

For example, compounds of formula I may be prepared by condensing an amino acid of formula VIII with a keto compound of formula IX in the presence of a reducing agent such as sodium cyanoborohydride in a solvent such as ethanol:

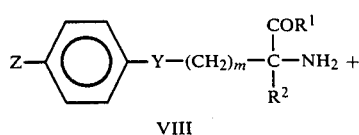

VIII

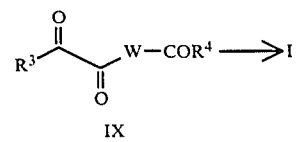

IX wherein Z, Y, $R^1$, $R^2$, $R^3$, $R^4$, m and W are as defined above.

Starting materials of formula VIII may be prepared by well known methods. An example of such a preparation is shown below, wherein 5-(4-[6-chloro-7-sulfamoyl-3,4-dihydro-1,1-dioxo-1,2,4-benzothiadiazinyl-3-)methoxy]benzyl)cysteine (formula XVI) is prepared, starting with 2-bromo-1,1-diethoxyethane and p-cresol:

Compounds of formula I wherein Y is $-CH_2-$, and Z is a group of formula VII, are preferably prepared by the reaction of an acid of formula XIX with an amine of formula XX:

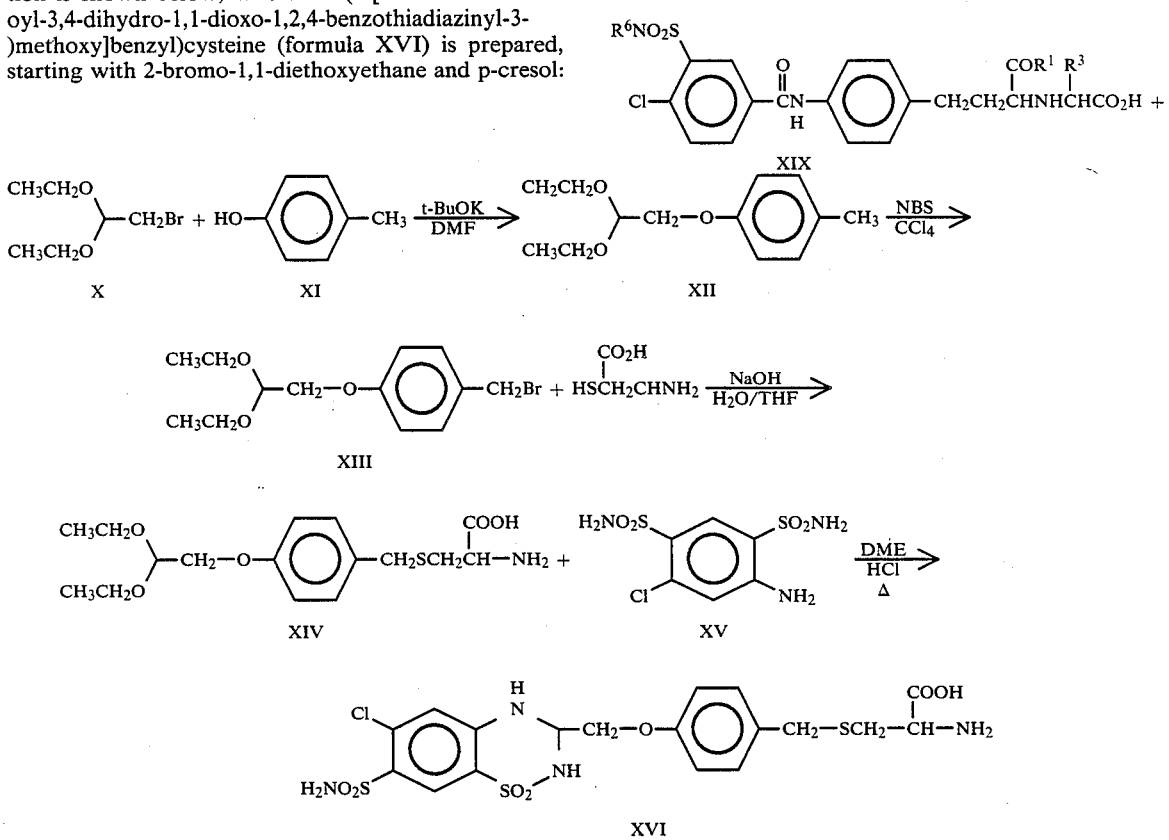

Starting materials of formula IX may be prepared by reacting an amino acid derivative VIII with an α-keto acid chloride XVII to give the substituted amino acid:

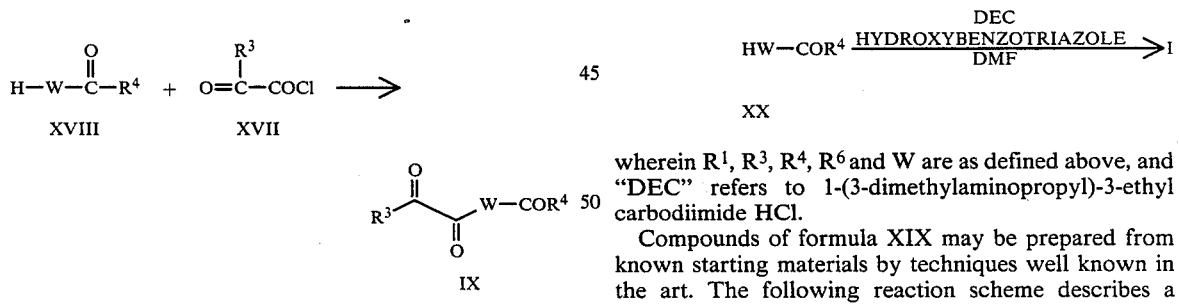

The reaction is carried out in an inert solvent such as methylene chloride in the presence of a base such as triethylamine or pyridine.

wherein $R^1$, $R^3$, $R^4$, $R^6$ and W are as defined above, and "DEC" refers to 1-(3-dimethylaminopropyl)-3-ethyl carbodiimide HCl.

Compounds of formula XIX may be prepared from known starting materials by techniques well known in the art. The following reaction scheme describes a method of preparing a compound of formula XIX (designated formula XIXa):

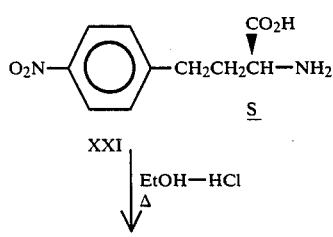

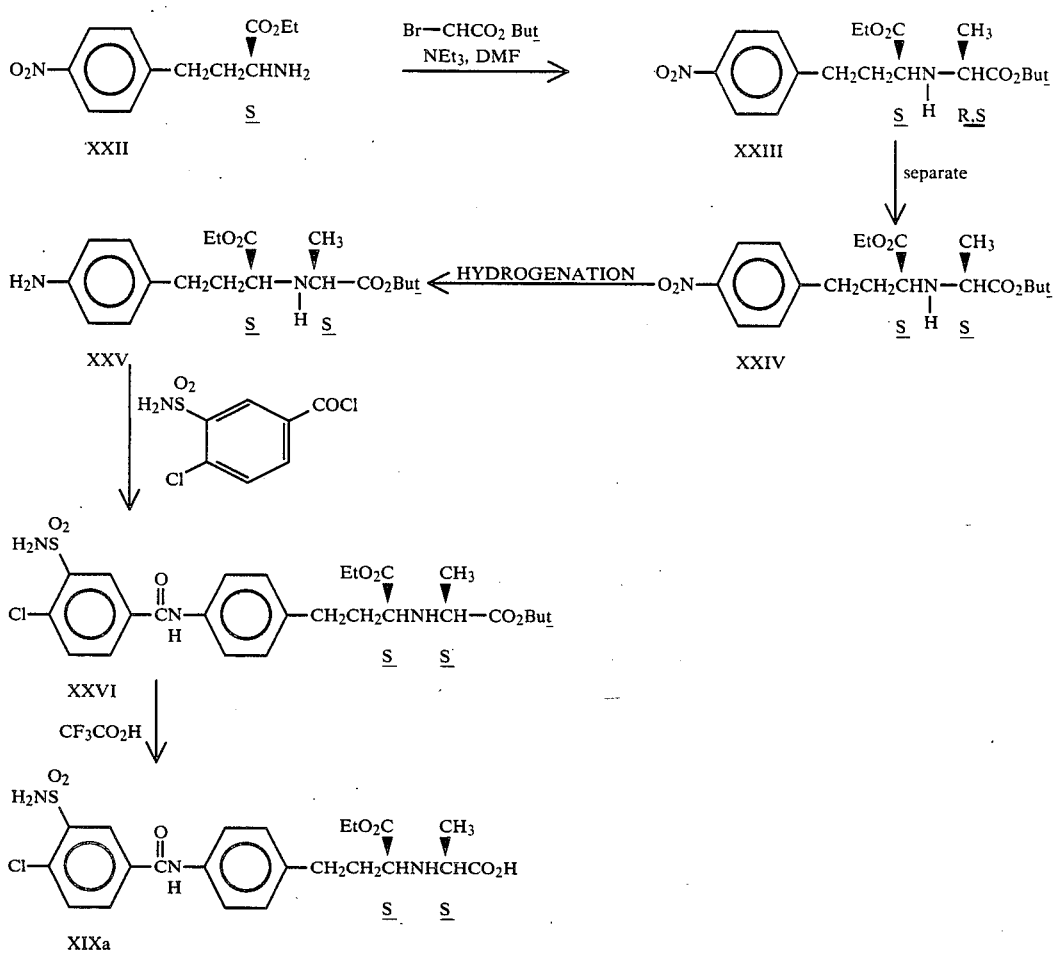

A preferred method for the conversion of compounds of formula XXII to XXIV in the reaction scheme above which eliminates the preparation of diastereomers of formula XXIII and their subsequent separation is to use the specific diastereomer t-butyl 2R-(trifluoromethanesulfonyloxy)propionate (triflate reagent). In this novel process, the single diastereomer of the triflate reagent reacts by nucleophillic displacement with the α-aminoacid ester (e.g., a compound of formula XXII) to give a high yield of the corresponding specific single diastereomer of the resulting monoamino dicarboxylic acid ester (e.g., a compound of formula XXIV).

Since the preferred compounds of formula I have an S-configuration at the carbon to which $R^3$ is attached the triflate reagent used herein is the 2-R diastereomer (see Preparation 4). However, the process is generally applicable to converting a broad range of α-aminoacid esters to the desired specific single diastereomer by using the appropriate triflate diastereomer. In place of the t-butyl ester of the triflate, other lower alkyl esters or the benzyl ester may be used.

The reaction proceeds at room temperature (i.e., 20°–50° C., preferably about 25° C.) in an inert solvent such as chloroform, dichloromethane, carbontetrachloride, benzene, toluene, or ethyl acetate in the presence of a base such as a tertiary amine (e.g., triethylamine or N-methylmorpholine). The reaction is complete in about 24 hours or less. The desired compound is recovered from the reaction mixture and purified by standard techniques. For example, the crude product is extracted into an organic solvent such as ether and concentrated to a crude oil, which is then purified by column chromatography to yield the desired specific diastereomer.

Carboxy-protected compounds of formula XX are prepared by methods well known in the art. See, for example, Neustadt et al. in European patent application No. 50,800, published May 5, 1982.

Alternatively, compounds of formula I wherein Y is —$CH_2$—, and Z is a group of formula VII may be prepared by the reaction of an acid chloride of formula XXVII with a dipeptide of formula XXVIII:

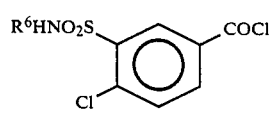 XXVII

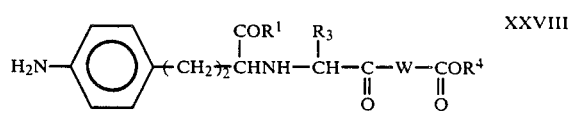 XXVIII wherein $R^1$, $R^3$, $R^4$, $R^6$ and W are as defined above.

Compounds of formula XXVII may be prepared by known methods.

Compounds of formula XXVIII may be prepared by well known methods, an example of which is shown in the following reaction scheme:

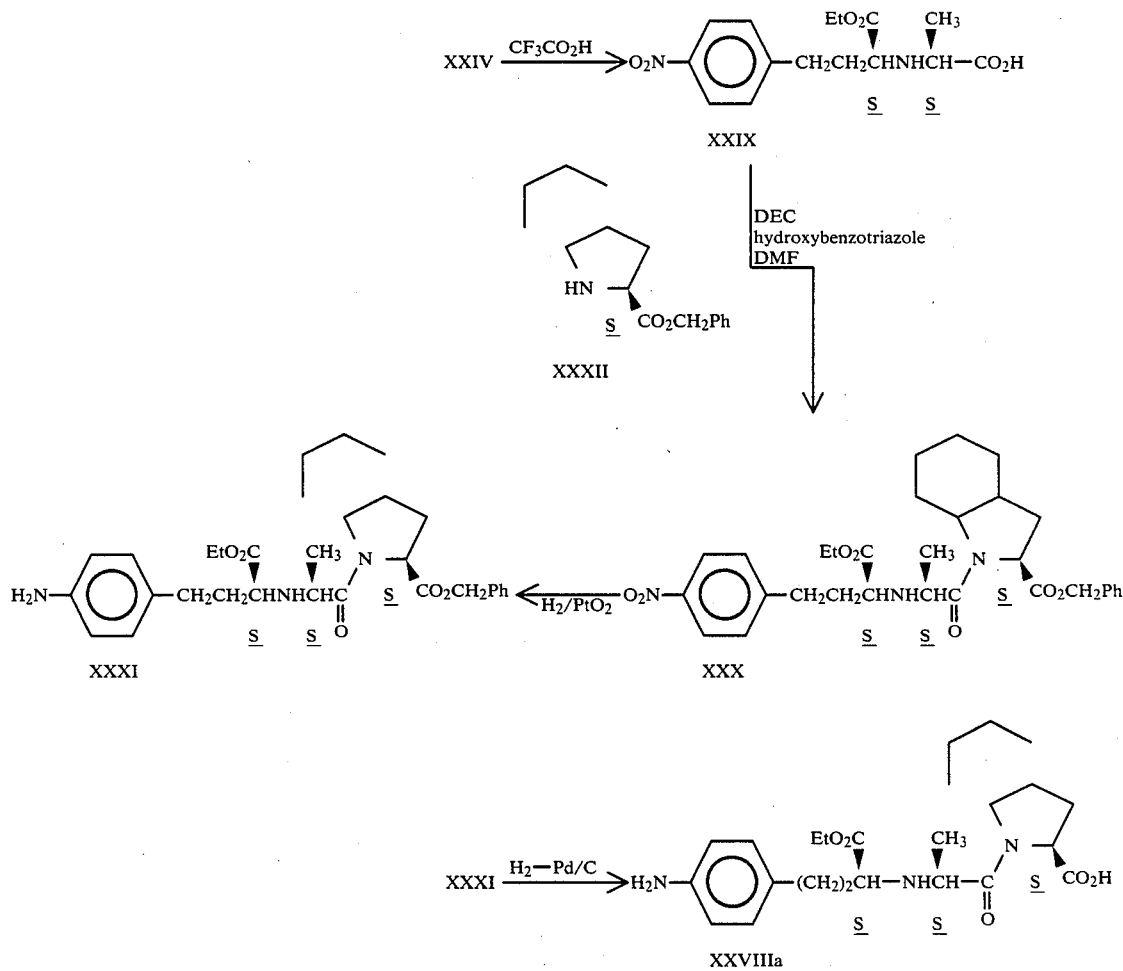

Alternatively, XXX may be hydrogenated directly to give XXVIIIa using a catalyst such as palladium on carbon.

Alternatively, XXXII may be reacted with a compound of formula XIXa to give a compound of formula I wherein $R^4$ is benzyloxy. The benzyloxy group may be then removed by hydrogenation with an appropriate catalyst such as palladium on carbon.

The known coupling methods above include amino group protection during the coupling reaction, for example by N-formyl, N-t-butoxycarbonyl and N-carbobenzyloxy groups, followed by their removal to yield compounds of formula I. Furthermore, the $COR^4$ function wherein $R^4$ is OH may be protected by removable ester groups such as benzyl, ethyl, t-butyl and the like.

The more complex esters at $R^1$ (i.e., $R^1$ is other than hydroxy or alkoxy) are most conveniently prepared by esterifying compounds of formula I wherein $R^1$ is hydroxy and $R^4$ is benzyloxy with the appropriate reagent, then removing the benzyl ester at $R^4$. For example, compounds of formula I where $R^1$ is hydroxy and $R^4$ is benzyloxy may be reacted with chloromethyl pivalate to obtain the corresponding pivaloyloxymethyl ester.

The pharmaceutical compositions of the invention are administered in the form of ophthalmic pharmaceutical compositions adapted for topical administration to the eye; such as solutions, suspensions, ointments and solid inserts. Formulations of the invention may contain from about 0.025% (w/v) to about 2.5% and especially about 0.1% to about 1.0% of a compound of formula I. As a unit dosage form, between about 12.50 µg to about 1.25 mg preferably 50 µg to 500 µg of such compound is applied to the human eye.

Where utilized herein, the term "controlling the elevated intraocular pressure" means the regulation, attenuation and modulation of increased intraocular tension, which is the primary diagnostic symptom of the disease glaucoma. The term also means that the diminution, in the otherwise elevated intraocular pressure, obtained by the practice of the invention is maintained for a significant period of time as, for example, between consecutive doses of the composition of the invention.

The (benzothiadiazine, benzamide and benzenesulfonyl)-phenyl-substituted carboxyalkyl dipeptide compounds of formula I may be employed in the composition and methods of the invention as the sole IOP lowering ingredient or may be used in combination (in the same or separate compositions) with other mechanistically distinct IOP lowering ingredients such as beta-adrenergic blocking agents, (e.g., timolol). For purposes of the present invention, the term beta-adrenergic blocker means a compound which by binding to beta adrenergic plasma membrane receptors reduces or eliminates sympathetic activity or blocks the effects of exogenously administered catecholamines or adrenergic drugs. See, for example, Weiner, N., Drugs That Inhibit Adrenergic Nerves and Block Adrenergic Receptors, in *The Pharmaceutical Basis of Therapeutics* (ed. A. G. Goodman, L. S. Goodman, A. Gilman), Macmillan Publishing, New York, 1980, 6th ed., pp. 188–197. Examples of preferred beta adrenergic blockers are bunolol (4-[2-hydroxy-3-[(1-methylethyl)amino]propoxy]benzeneacetamide), metoprolol (1-[4-(2-methoxyethyl)phenoxy]-3-[(1-methylethyl)amino]-2-propanol), nadolol (5-[3-[(1,1-dimethylethyl)amino]-2-hydroxypropoxy]-1,2,3,4-tetrahydro-2,3-naphthalenediol), pindolol (1-(1H-indol-4-yloxy)-3-[(1-methylethyl)amino]-2-propanol), propranolol (1-[(1-methylethyl)amino]-3-(1-naphthalenyloxy)-2-propanol), timolol (1-[(1,1-dimethylethyl)amino]-3-[(4-morpholinyl-1,2,5-thiadiazol-3-yl)oxy]-2-propanol), labetalol (2-hydroxy-5-[1-hydroxy-2-[(1-methyl-3-phenylpropyl)amino]ethyl]-benzamide), betaxolol (1-[4-[2-(cyclopropylmethoxy)ethyl]-phenoxy]-3-[(methylethyl)amino]-2-propanol), carteolol (5-[3-[(1,1-dimethylethyl)amino]-2-hydroxypropoxy]-3,4-dihydro-2(1H)-quinolinone), and dilevalol ([R-(R,R)]-2-hydroxy-5-[1-hydroxy-2-[(1-methyl-3-phenylpropyl)amino]ethyl]-benzamide 4-methylbenzenesulfonate salt), "and pharmaceutically acceptable salts and isomers thereof".

The usefulness of beta adrenergic blockers for lowering intraocular pressure is known in the art. Thus, the beta adrenergic blocker timolol, is currently approved by the U.S. Food and Drug Administration for topical use as a treatment for glaucoma. It is marketed in two dose strengths, i.e., 0.25% and 0.5%. As previously stated, this agent must be used with caution in a defined patient population because of recognized untoward side effects (see Physicians Desk Reference for Ophthalmology, 11th edition, 1983, p. 126, Medical Economics Co. Inc., Oradell, N.J. 07649).

As one aspect of the present invention, it is contemplated that a reduction in intraocular pressure equivalent to that obtained by use of a beta-blocker, e.g., the approved clinical dose of the beta-blocker timolol, may be obtained by use of a lower dose of beta-blocker when such lower dose is combined with an effective amount of a compound of formula I. It is anticipated that the use of the diminished dosage of beta-blocker, e.g., timolol, will result in a reduction of severity and frequency of timolol-like related side effects.

For purposes of this combination treatment modality, the beta-blocker and compound of formula I are preferably administered simultaneously as one composition in one pharmaceutical dosage form, but they may be applied as separate topical compositions, if desired. When applied as part of a composition including a compound of formula I, the beta adrenergic blocker may comprise from about 0.01% to about 1.0% of the composition of the invention. The preferred ranges of the components in the composition of the invention in unit dosage form are as follows:

Beta adrenergic blocker: from 5 μg to 250 μg (Benzothiadiazine, benzamide and benzenesulfonyl)-phenyl-substituted carboxyalkyl dipeptide compound: from 50 μg to 500 μg.

When applied in separate compositions, the beta-adrenergic blocker and compound of formula I may be included in such compositions in the same ranges. The individual dosage requirements, i.e., the amount of each dose and the frequency of administration, may vary depending on the severity of the disease and the response of the patient.

Since the composition of the invention and the composition including the beta-adrenergic blocker can be administered separately, the invention also relates to combining separate pharmaceutical compositions in kit form, that is, combining two separate units, an inventive pharmaceutical composition and a topical pharmaceutical composition including a beta-adrenergic blocker, in a single package. A particular advantage of the kit resides in the ability to provide a combination of an inventive composition which can be administered once or twice a day and a topical beta-adrenergic blocker composition which may be administered as necessary or desired.

Those skilled in the art will appreciate that the "intraocular pressure reducing concentration" for such combination therapy will consist of a range of concentrations (doses), and that there will be a lower limit to said concentration below which, the present invention will not operate. For purposes of this invention, this lower limit or minimum dosage may be considered to be about 5% of the effective dose (threshold dose) of the particular component. The intraocular pressure reducing concentration that is actually utilized, whether for a compound defined in formula I or for a particular beta adrenergic blocker, will depend on, inter alia, the potency of each particular material, the combination being administered and the age, size and condition of the patient being treated as well as on the severity of the disease state.

We also contemplate that the elevation in IOP associated with the clinical ophthalmic and systemic use of anti-inflammatory steroids can be reduced by the administration of a composition of the present invention. In particular, an increase in IOP is most often associated with the administration of steroidal anti-inflammatory agents. Anti-inflammatory steroids include hydrocortisone, cortisone, prednisolone, prednisone, dexamethasone, methylprednisolone, triamcinolone, betamethasone, alclometasone, flunisolide, beclomethasone, clorocortolone, diflorasone, halcinonide, fluocinonide, flucinolone, desoximetasone, medrysone, paramethasone, 9,21-dichloro-17-[(2-furanylcarbonyl)oxy]-11-hydroxy-16α-methyl-pregna-1,4-diene-3,20-dione and fluorometholone, and their pharmaceutically acceptable salts and esters. Preferred steroids are hydrocortisone, prednisolone, dexamethasone, betamethasone, beclomethasone, medrysone and fluoromethalone and their pharmaceutically acceptable salts and esters. This rise in IOP may occur with all modes of administration of the drugs, including systemic (usually oral), local injection (e.g., depot injection), and especially with ophthalmic topical or intravitreal administration. The composition of the present invention may be administered following steroid treatment to lower elevated IOP, or may be co-administered with the steroid to suppress the IOP-raising effect of the steroid while not interfering with the anti-inflammatory activity of the steroid.

It is further contemplated that any possible combination of dosage forms may be used to administer the combination, e.g., oral steroid/topical composition of the invention, topical steroid/oral composition of the invention, oral steroid/oral composition of the invention, topical steroid/topical composition of the invention, and locally injected steroid/topical composition of the invention, although a preferred combination comprises a steroid and a topical composition of the invention. For ophthalmic use, a combination of a topical steroid and a topical composition of the invention is preferred. More preferred is a topical ophthalmic pharaceutical dosage form comprising both a steroid and a composition of the invention. Such compositions or combinations can be employed in a method for reducing and controlling the elevated IOP associated with ophthalmic and systemic use of steroidal anti-inflammatory agents, which method comprises administering to a mammal effective amounts of a steroid and a composition of the invention, either separately or in the same pharmaceutical composition.

Since the present invention relates to treatment with a combination of a composition of the invention and a steroidal anti-inflammatory agent wherein the inventive composition and steroid may be administered separately, the invention also relates to combining separate pharmaceutical compositions in kit form, that is, combining two separate units, an inventive pharmaceutical composition and a steroid pharmaceutical composition, in a single package. Preferred components of the kit comprise a topical ophthamological pharmaceutical composition including a compound of formula I and a pharmaceutically acceptable steroid composition. More preferred components of the kit are a topical ophthamological inventive pharmaceutical composition including a compound of formula I and a topical ophthamological steroid pharmaceutical composition. A particular advantage of the more preferred embodiment of the kit resides in the ability to provide a combination of an inventive composition which can be administered once or twice a day and a steroid composition which may be administered as frequently as once each hour.

While the mechanism by which corticosteroids provide anti-inflammatory activity is unknown, their ability to provide relief from inflammatory symptoms is widely recognized. See, for example, Haynes, R. C., Jr., and Murad, F., "Adrenocorticotropic Hormone; Adrenocortical Steroids and Their Synthetic Analogs, Inhibitors of Adrenocortical Steroid Biosynthesis" in *The Pharmacological Basis of Theraputics* (ed., A. G. Gilman, L. S. Goodman, A. Gilman), Macmillan Publishing, New York, 1980, 6th ed., pp. 1470–1492, n.b. pg. 1490–1491.

In this combination treatment modality, topical formulations of the invention may combine the following amounts of each inventive composition and steroidal constituent, or each constituent may be administered separately:

A compound of formula I from about 0.025% (w/v) to about 2.5% and especially about 0.1% to about 1.0% of medicament. As a unit dosage form, an amount of a compound of formula I of from about 12.5 $\mu$g to about 1.25 mg, and preferably about 50 $\mu$g to about 500 $\mu$g of the active component is applied to the human eye. Individual dosage requirements, i.e., the amount of each dose and the frequency of administration, will depend on the potency of the particular composition of the invention, the severity of the increase in IOP and the response of the patient.

Steroid from about 0.05 to about 1.5 (w/v%) of medicament. As a unit dosage form, an amount of steroid from between 20 $\mu$g to 600 $\mu$g of the active composition is applied to the human eye. Individual dosage requirements, i.e., the amount of each dose and the frequency of administration will depend on the potency of the particular steroid, the severity of the disease and the response of the patient. Approximate ranges for such steroids are well known to those skilled in the art. The particular steroid selected will determine which inventive composition and concentration thereof to select for use in a combination preparation.

In one embodiment of the invention, both active ingredients, i.e., inventive composition and steroid, will be administered simultaneously and be contained in one pharmaceutical dosage form, each component being present in the dosage form in its own respective preferred concentration. When the steroid is administered systemically or topically other than in an ophthalmological composition, the concentration of the steroid in the composition and the unit dosage weight may vary considerably, depending as above on such factors as the potency of the steroid, its onset and duration of action as well as the severity of the disease, and the response of the patient. Appropriate dosage ranges for systemic and topical administration of each steroid are well known in the art.

Those skilled in the art will know that for solutions and suspensions, a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain 0.125 mg or 125 $\mu$g of active.

The IOP-lowering effects of the compositions employed in the invention may be measured by the procedure described by Watkins et al., J. Ocular Pharmacol. 1 (2): 161–168, 1985.

To prepare suitable dosage forms, the active compositions may be conveniently admixed with a non-toxic pharmaceutically acceptable carrier suitable for topical ophthalmolgic administration. Typical of such pharmaceutically acceptable carriers are, for example, water, mixtures of water and water-miscible solvents such as lower alkanols or vegetable oils, petroleum based jelly, and including also from 0.5 to 5% by weight of ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acids salts; ethylacrylates; polyacrylamides; natural products such as gelatin, alginates, pectins, tragacanth, karaya, chondrus, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, neutralized carbomer and xanthan gum; and mixtures of these polymers. The pharmaceutical preparation may also contain non-toxic auxiliary substances such as emulsifying, preserving, wetting, bodying agents and the like, as for example, polyethylene glycols 200, 300, 400, 600, 1,000, 1,500, 4,000, 6,000 and 10,000; antibacterial components such as quarternary ammonium compounds; phenylmercuric salts known to have cold sterilizing properties and which are non-injurious in use; thimerosal; methyl and propyl paraben; benzyl alcohol; phenyl ethanol;

buffering ingredients such as alkali metal chloride, borate, acetate, gluconate buffers; antioxidants such as sodium metabisulfite, butylated hydroxyanisol (BHA), butylated hydroxytoluene (BHT) and the like; and other conventional ingredients such as sorbitan monolaurate, triethanolamineoleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharamaceutical preparation may also be in the form of a solid insert. For example, one may use a solid water soluble polymer as the carrier for the medicament. Inserts that are known in the art that are suitable for this use include those described in British Pat. No. 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include additional therapeutic agents in addition to the inventive composition. For example antibiotics, anesthetics as well as other IOP-lowering agents may be present.

The following examples are intended to illustrate, but not to limit, the present invention. In such examples, Compound A refers to 1-[N-[1-(S)-ethoxycarbonyl-3-[4-(6-chloro-3,4-dihydro-1,1-dioxo-7-sulfamoyl-2H-1,2,4-benziothiadiazine)acetamidephenyl]propyl]-(S)-alanyl]-cis,syn-octahydro-1H-indole-2(S)-carboxylic acid. It is contemplated however, that this compound may be replaced by equally effective quantities of other compounds within the scope of formula I.

EXAMPLE 1

| Topical Solution: Ingredients | mg/ml |
| --- | --- |
| Compound A | 10.0 |
| Dibasic Sodium Phosphate | 10.4 |
| Monobasic Sodim Phosphate | 2.4 |
| Chlorobutanol | 5.0 |
| Hydroxypropyl methylcelluose | 5.0 |
| Sodium Hydroxide or Hydrochloric Acid | q.s. ad pH 7.4 |
| Sterile Water | q.s. ad 1.0 ml |

Mix the ingredients under sterile conditions and using standard techniques to obtain the ophthamological solution.

EXAMPLE 2

| Topical Solution: Ingredients | mg/ml |
| --- | --- |
| Compound A | 10.0 |
| Timolol | 5.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sodium Hydroxide or Hydrochloric acid | q.s. ad pH 7.4 |
| Sterile Water | q.s. ad 1.0 ml |

Mix the ingredients under sterile conditions and using standard techniques to obtain the ophthamological solution.

In the above example, other beta-adrenergic blocking agents may be used, such as bunolol.

EXAMPLE 3

| Topical Solution: Ingredients | mg/ml |
| --- | --- |
| Compound A | 10.0 |
| Dexamethasone Sodium Phosphate | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sodium Hydroxide or Hydrochloric Acid | q.s. ad pH 7.4 |
| Sterile Water | q.s. ad 1.0 ml |

Mix the ingredients under sterile conditions and using standard techniques to obtain the ophthamological solution.

Again, other compounds of formula I and steroids can be employed in place of those listed in the formulation above, with the particular amounts varying depending on the drugs employed.

The following examples further illustrate the preparation of compounds employed in the practice of the invention.

PREPARATION 1

1-Pyruvoyl-cis,syn-Octahydro-1H-Indole-2(S)-Carboxylic Acid

A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g of 10-d-camphorsulfonic acid in 1 liter of warm ethyl acetate and add a solution of 86 g of the product of part A in 1 liter of ethyl acetate. Allowing the mixture to crystallize, heat to reflux, cool to room temperature, and filter. Recrystallize the filter cake from a mixture of 500 ml of isopropanol and 1800 ml ethyl acetate, filter and dry the crystals to obtain 2(S)-carboethoxy-cis,syn-octahydro-1H-indole, d-10-camphorsulfonate, m.p. 192°–193° C.

C. Slurry 10 g of the product of part B in 1 liter of ether, adjust to pH 11 with aqueous sodium hydroxide, and stir for 5 minutes. Wash the organic layer with sodium chloride solution, dry over magnesium sulfate, filter, and evaporate in vacuo at room temperature to obtain 2(S)-carboethoxy-cis,syn-octahydro-1H-indole as a colorless oil. Dissolve the resultant oil in 50 ml of methanol containing 23 ml of 1N sodium hydroxide, stir at 25° C. for 30 minutes, adjust to pH 7 with 1N hydrochloric acid, and evaporate the solvent to give cis,syn-octahydro-1H-indole-2(S)-carboxylic acid.

D. Cool 23 ml of benzyl alcohol to 0° C. under nitrogen and add 5.95 g of thionyl chloride dropwise over 15 minutes, maintaining the temperature at 0° C. Add the product of part C, stir for 1 hour at 0° C., then stir for 24 hours at room temperature. Pour the resulting mixture into 500 ml of ether, stir 1 hour under nitrogen, then allow to stand under nitrogen until the solution is clear. Decant the supernatant, wash the precipitate with 25 ml of ether, then slurry the precipitate in 200 ml of ether and adjust to pH 8–9 with 1-N sodium hydroxide. Stir 5 minutes, wash the organic layer with sodium chloride solution, dry over magnesium sulfate, filter and evaporate in vacuo at room temperature to obtain cis,-syn-octahydroindole-2(S)-carboxylic acid, benzyl ester as a colorless oil (TLC in ether: one spot, Rf 0.3).

E. To 26 g of the product of part D in 100 ml of dichloromethane and 7.8 ml of pyridine add 11.0 g of pyruvoyl chloride and stir the resulting mixture at room temperature. Extract the reaction mixture with water and dry the organic layer over magnesium sulfate. Concentrate the dichloromethane solution in vacuo and distill the residue to give 1-pyruvoyl-cis,syn-octahydro-1H-indole-2(S)-carboxylic acid, benzyl ester.

F. To 20 g of the product from part E in 400 ml of ethanol, add 2.0 g of 10% palladium-on-charcoal and hydrogenate at 50 psi at room temperature. Filter the resulting mixture and concentrate the filtrate in vacuo to give the title compound.

PREPARATION 2

1-{N-[1(S)-Ethoxycarbonyl-2-(4-aminophenyl)ethyl]-(S)-alanyl}-cis,syn-octahydro-1H-indole-2(S)-carboxylic acid Method I A. To a solution of 4-nitrophenylalanine, ethyl ester, hydrochloride (54.0 g) in dry dimethylformamide (400 ml), add t-butyl 2-bromopropionate (112.3 g) and triethylamine (76 ml) and heat the resulting mixture at 70° for 18 hours under a nitrogen atmosphere. Pour the reaction mixture into water and extract with methylene chloride (6×300 ml). Combine the organic layers, dry over magnesium sulfate and concentrate in vacuo to give a liquid (contains DMF). Chromatograph this liquid on a Prep 500 (3 silica gel cartridges) using hexane (8 l) then hexane:ethylacetate 4:1 and isolate N-[1(S)-ethoxycarbonyl-2-(4-nitrophenyl)ethyl]-(R)alanine, t-butyl ester, $[\alpha]_D^{26} = +24.7°$ (methanol), and N-1(S)-ethoxycarbonyl-2-(4-nitrophenyl)ethyl]-(S)alanine, t-butyl ester.

B. Add cold trifluoroacetic acid (600 ml) (ice bath) to N-[1(S)-ethoxycarbonyl-2-(4-nitrophenyl)ethyl](S)-alanine, t-butyl ester (25.5 g) and stir the resulting mixture at room temperature under a nitrogen atmosphere for 4 hours. Concentrate the solution in vacuo to give a viscous oil. Triturate the viscous oil with hexane (3 l) and then ether to yield N-[1(S)-ethoxycarbonyl-2-(4-nitrophenyl)ethyl]-(S)-alanine.

C. To a solution of the product of Step B (17.84 g), cis,syn-octahydro-1H-indole-2(S)-carboxylic acid, benzyl ester (11.50 g), and triethylamine (4.46 g) in dimethylformamide (450 ml) at 0°–5° under a nitrogen atmosphere, add 1-hydroxybenzotriazole (6.76 g) and 1-(3-dimethylaminopropyl)-3-ethylcarbodiimide, hydrochloride (16.13 g). Stir the reaction mixture at 0°–5° for 25 minutes and then at room temperature for 90 minutes. Concentrate the reaction mixture in vacuo and partition between dichloromethane and saturated sodium bicarbonate solution. Dry the organic layer over magnesium sulfate and concentrate in vacuo to give a viscous oil which contains 1-{N-[1(S)-ethoxycarbonyl-2-(4-nitrophenyl)ethyl]-(S)-alanyl}-cis,syn-octahydro-1H-indole-2(S)-carboxylic acid, benzyl ester.

D. Hydrogenate the product from Step C above in absolute ethanol (250 ml) in the presence of 10% palladium on carbon at 60 psi in a Parr Shaker Apparatus. Remove the catalyst by filtration through celite and concentrate the filtrate in vacuo to give a foam. Chromatograph the foam on the Prep 500 (3 cartriges) using chloroform:methanol:ammonium hydroxide 200:30:5 as eluant to give the title compound $[\alpha]_D^{26} = -44.0°$ (MeOH).

Method II

A. To a solution of 4-nitrophenylalanine, ethylester, hydrochloride (2.3 g) in dichloromethane (10 ml), add triethylamine (2.55 ml) and then t-butyl 2(R)-(trifluoromethanesulfonyloxy)propionate (2.80 g) (see Preparation 4) in dichloromethane (10 ml). Stir the resulting solution at room temperature for 20 hours. Concentrate the reaction mixture, add diethyl ether and extract with salt solution. Dry over magnesium sulfate and concentrate the ether solution in vacuo to give an oil. Place the oil on a column of silica gel (100 ml, 60–200 mesh) and elute with diethyl ether:hexane 60:40 to give N-[1(S)-ethoxycarbonyl)-2-(4-nitrophenyl)ethyl]-(S)-alanine, t-butyl ester.

B. to D. Proceed as described in Method I.

PREPARATION 3

1-{N[1(S)-Ethoxycarbonyl-3-(4-aminophenyl)propyl]-(S)-alanyl}-cis,syn-octahydro-1H-indole-2(S)-carboxylic acid Method I A. To a solution of 2-acetamido-4-(4-nitrophenyl)-butyric acid (57.65 g) in hot 95% ethanol (1000 ml) add d-(+)-α-methylbenzylamine (25.2 g) in hot 95% ethanol (125 ml), cool the solution slowly and keep at room temperature 18 hours. Collect the solid and wash with cold 95% ethanol, and dry to give an orange-yellow solid. Recrystallize this solid from 95% ethanol treated with charcoal to give 2(S)-acetamido-4-(4-nitrophenyl)-butyric acid, d-(+)-α-methylbenzyl amine salt $[\alpha]_D^{26} = +45.6$ (MeOH), m.p. 211°–213° C.

B. Suspend the product of part A (29.00 g) in ether (500 ml) and add 1N NaOH (150 ml). Separate the aqueous solution and wash with ether. Cool the aqueous solution in an ice-NaCl bath, add concentrated hydrochloric acid to pH 1 and stir the resulting mixture for 1 hour. Remove 2(S)-acetamido-4-(4-nitrophenyl)butyric acid, a white solid, $[\alpha]_D^{26} = +33.9°$ (MeOH), m.p. 266° C.

C. Treat the compound prepared in part B above (18.65 g) with 6N hydrochloric acid (700 ml) and heat the resulting mixture under reflux for 2.5 hours. Concentrate the solution in vacuo to give 2(S)-amino-4-(4-nitrophenyl)butyric acid, hydrochloride, a solid, m.p. 186°–189° C., $[\alpha]_D^{26} = +46.9°$ (MeOH).

D. Heat the compound prepared in part C (19.30 g) in absolute ethanol saturated with hydrogen chloride acid (400 ml) under reflux for 1½ hour. Remove the solvent in vacuo and triturate the residue with ether to give 2(S)-amino-4-(4-nitrophenyl)butyric acid, ethyl ester, hydrochloride, a white solid m.p. 288.5° $[\alpha]_D^{26} + 40.6°$ (MeOH).

E. Treat the compound prepared in part D (18.00 g) in dry dimethylformamide (250 ml) with t-butyl 2-bromopropionate (35.20 g) and triethylamine (18.90 g) as extract with dichloromethane (2×1:1). Dry the organic layer over magnesium sulfate and concentrate in vacuo to give a viscous oil. Chromatograph this oil on the Prep 500 (2cartridges) using ethyl acetate:hexane 3:20 and then 1:1 and isolate 1-{N[1(S)-ethoxycarbonyl-3-(4-nitrophenyl)propyl]-(S)-alanyl}-cis,syn-octahydro-1H-indole-2(S)-carboxylic acid, benzyl ester.

H. Hydrogenate the product of part G (4.69 g) in absolute ethanol (250 ml) in the presence of 5% palladium-on-charcoal (0.50 g) at 60 psi in a Parr Shaker Apparatus. Remove catalyst by filtration and concentrate the filtrate to give the title compound, a foam $[\alpha]_D^{26} = -29.7°$ (MeOH).

Method II

A. to D. Proceed as described in Method I.

E. Treat the product of part D as described in Preparation 2, Method II, part A to obtain N-[1(S)-ethoxycarbonyl]-3-(4-nitrophenyl)propyl]-(S)-alanine, t-butyl ester.

F. to H. Proceed as described in Method I.

PREPARATION 4 t-Butyl 2R-(Trifluoromethanesulfonyloxy)Propionate

A. Add 2S-(p-toluenesulfonyloxy)propionic acid (4.4 g) to a cold solution of 10 ml isobutylene and 0.4 ml concentrated sulfuric acid in 30 ml methylene chloride in a pressure vessel, seal, and agitate at room temperaure for 48 hours. Pour into 50 ml 15% sodium carbonate solution, dry over magnesium sulfate and concentrate to obtain t-butyl 2S-(p-toluenesulfonyloxy)propionate as an oil (NMR 1.37). Distilled material (Kugelrohr, 120°) has $[\alpha]D^{26} = -45.9°$ (EtOH, c=1).

B. Combine the product of part A (100 g) with acetic acid (40.0 g) and triethylamine (67.2 g) in 200 ml dry DMF. Heat at 65° for 20 hours. Partition with 2 l each ether and water, and wash the ether with citric acid, then with sodium bicarbonate solution. Dry and concentrate the ether solution to obtain t-butyl 2R-acetoxypropionate as a colorless liquid, bp 50° C./0.1 mm.

C. Combine the product of part B (62.6 g) with ethylenediamine (11.6 g) and heat at 70° for 24 hours. Allow to cool, add 300 ml ether and filter. Wash the ether with water, 10% citric acid, and then in sodium bicarbonate solution. Dry and concentrate the ether solution to leave a colorless oil. Crystallize from hexane at −20° to give t-butyl 2R-hydroxypropionate as white needles, m.p. 41°-2° C.

D. Combine the product of part C (7.3 g) with pyridine (4.0 g) in 50 ml methylene chloride. Cool to −5° C., and add dropwise a solution of trifluoromethanesulfonic anhydride (14.1 g) in 25 ml methylene chloride. Allow the reaction to reach room temperature, then wash successively with water, 1N sulfuric acid and 1N sodium bicarbonate solution. Dry and concentrate the methylene chloride solution to leave the title compound as a colorless oil.

NMR (in CDCl3)=5.10 q; 1.73 d; 1.50 s.

EXAMPLE 4

1-{N-[(S)-Ethoxycarbonyl-2-[4-(3-sulfamoyl-4-chlorobenzamido)phenyl]ethyl]-(S)-alanyl}-cis,syn-octahydro-1H-indole-2(S)-carboxylic acid To a 0°-5° C. solution of the product of Preparation 2 (2.00 g) in anhydrous tetrahydrofuran (100 ml) and triethylamine (0.94 g), add a solution of 4-chloro-3-sulfamoylbenzoylchloride (1.61 g) in anhydrous tetrahydrofuran (10 ml) over a period of 30 minutes. Stir the resulting mixture for 15 minutes at 0°-5° and then at room temperature for 18 hours. Filter the reaction mixture and concentrate the filtrate in vacuo to give a residue. Chromatograph the residue on the Prep 500 (1 cartridge) using chloroform:methanol:ammonium hydroxide 200:30:5 as eluant to give the title compound, a foam, $[\alpha]_D^{26} -16.1°$ (MeOH).

In a similar manner, using appropriate starting materials, prepare the following:

1-{N-[1(S)-ethoxycarbonyl-2-[4-(4-chloro-3-N-methylsulfamoylbenzamido)phenyl]ethyl]-(S)-alanyl}-cis,-syn-octahydro-1H-indole-2(S)-carboxylic acid, $[\alpha]_D^{26} = -18.7°$ (methanol).

1-{N-[1(S)-ethoxycarbonyl-3-[4-(2-hydroxy-4-chloro-5-sulfamoylbenzamido)phenyl]ethyl]-(S)-alanyl}-cis,-syn-octahydro-1H-indole-2(S)-carboxylic acid, $[\alpha]_D^{26} = -18.1°$ (methanol).

EXAMPLE 5

1-{N-[1(S)-Carboxy-2-[4-(4-chloro-3-sulfamoylbenzamido)phenyl]ethyl]-(S)-alanyl}-cis,syn-octahydro-1H-indole-2(S)-carboxylic acid To the product of Example 4 (0.35 g) add 0.5N NaOH (5ml) and stir at room temperature for 1 hour. Add Bio-Rad Resin (AG 50W-X3, 100–200 mesh, hydrogen form) and then add to a column of the same resin. Elute with water (200 ml) and then water:pyridine 96:4. Concentrate the desired fractions to give the title compound. $[\alpha]_D^{26} = -7.0°$ (MeOH).

In a similar manner, prepare 1-{N[1(S)-carboxyl-2-[4-(4-chloro-3-N-methylsulfamoylbenzamido)phenyl]ethyl]-(S)-alanyl}-cis,syn-octahydro-1H-indole-2(S)-carboxylic acid, $[\alpha]_D^{26} = 8.9°$ (methanol).

EXAMPLE 6

1-{N-[1(S)-Ethoxycarbonyl-3-[4-(4-chloro-3-sulfamoylbenzamido)phenyl]propyl]-(S)-alanyl}-cis,syn-octahydro-1H-indole-2(S)-carboxylic acid To a 0°-5° solution of the compound of Preparation 3 (1.50 g) in anhydrous tetrahydrofuran (100 ml) and triethylamine (0.68 g), add a solution of 4-chloro-3-sulfamoylbenzoylchloride (1.11 g) and treat as described in Example 4, except use chloroform (2 l) and then chloroform:methanol:ammonium hydroxide 100:30:5 as eluants and isolate the title compound, a foam $[\alpha]_D^{26} = -9.1$ (methanol).

In a similar manner using appropriate starting materials, prepare 1-{N-[1(S)-Ethoxycarbonyl-3-[4-(4-chloro-3-N-methylsulfamoylbenzamido)phenyl]propyl]-(S)-alanyl}cis,syn-octahydro-1H-indole-2(S)-carboxylic acid.

EXAMPLE 7

1-{N-[1(S)-Carboxy-2-([4-[(6-Chloro-3,4-Dihydro-7-Sulfamyl-2H-1,2,4-Benzothiadiazin-3-yl-1,1-Dioxide)-Methyloxy]Phenyl]Methylthioethyl]-(S)-Alanyl}-cis,-syn-Octahydro-1H-Indole-2(S)-Carboxylic Acid A. Combine bromoacetaldehyde diethylacetal (19.7 g) and p-cresol (10.8 g) in dry dimethylformamide (DMF) (100 ml) and stir. Add potassium t-butoxide (9.6 g) and continue stirring for 24 hours, then evaporate the DMF in vacuo. Partition the resultant residue between ethyl acetate and water. Separate the organic layer, wash with 10% aqueous sodium hydroxide followed by brine, then dry the organic layer over sodium sulfate and filter. Evaporate the solvent in vacuo and purify the crude product on a silica gel column to obtain 4-[2,2-diethoxy)ethoxy]toluene:

NMR δ=1.12 (6H, t, CH3); 2.15 (s, 3H, —CH3); 3.55 (q, 4H, CH2—O); 3.90 (d, 2H, CH2—phenyl); 4.77 (t, 1H, —CH2—); and 6.80 (m, 4H, Ar).

B. Combine N-bromosuccinamide (0.877 g) and the product of Step A (1 g) in carbon tetrachloride (20 ml)

and stir at reflux for 18 hours. Filter the resultant solid and evaporate the solvent in vacuo to obtain 4-[(2,2-diethoxy)ethoxy]benzyl bromide:

NMR=1.10 (t, 6H, CH); 3.59 (q, 4H, —OCH$_2$); 3.86 (d, 2H, C—CH$_2$O); 4.31 (s, 2H, CH$_2$—Br); 4.70 (t, 1H, —CH—); 7.00 (m, 4H, Ar).

C. Combine methyl alcohol (20 ml) and 19M sodium hydroxide (10 ml). Add L-cysteine (0.1 g), stir for 15 minutes, then add the product of Step B and stir at room temperature overnight. Adjust the resultant solution to approx. pH 7 and filter the resultant solid. Wash the solid with ether and dry under vacuum to obtain (S)-[4-[(2,2-diethoxy)ethoxybenzyl]cysteine.

D. Dissolve 4-amino-6-chloro-1,3-benzenedisulfonamide (0.74 g) in dimethoxyethane (10 ml), add the product of Step C (0.99 g), stir while heating to reflux, and add 2 drops of concentrated hydrochloric acid. Reflux 4 hours, then evaporate the solvent in vacuo. Wash the resultant solid with ether and dry under vacuum to obtain S-[4-[(6-chloro-3,4-dihydro-7-sulfamyl-2H-1,2,4-benzothiadiazin-3-yl-1,1-dioxide)methoxy]benzyl]-L-cysteine.

E. React 0.02 moles of the product of part D in 20 ml of tetrahydrofuran with 0.02 moles of the product of Preparation 1 and add 20 ml of molecular sieves 4 A (Rohm and Haas). Stir the resulting mixture for 4 hours, add 12 g of sodium cyanoborohydride in 20 ml of methanol and stir the reaction mixture 20 hours. Filter, concentrate to dryness, and partition the residue between water and dichloromethane. Absorb the aqueous phase on strong acidic ion-exchange resin and elute with 4% pyriding in water. Separate the isomers on a column of silica gel using CHCl$_3$:isopropanol:7% ammonium hydroxide 1:1:1 (organic phase) as eluant to give the title compound.

EXAMPLE 8

1-{N-[1(S)-Ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanyl}-cis,syn-octahydro-1H-indole-2(S)-carboxylic acid A. Hydrogenate a solution of N-[1(S)-ethoxycarbonyl-2-(4-nitrophenyl)ethyl]-(S)-alanine, t-butyl ester (20.0 g) (see Preparation 2, IA) in absolute ethanol (500 ml) in the presence of 10% palladium on carbon (1.5 g) at 50 psi in a Parr shaker apparatus. Remove the catalyst by filtration and concentrate the filtrate in vacuo to give N-[1(S)-ethoxycarbonyl-2-(4-aminophenyl)ethyl]-(S)-alanine, t-butyl ester.

B. To a solution of the product of part A in dimethylformamide (150 ml), add 6-chloro-3,4-dihydro-1,1-dioxo-7-sulfamoyl-1,2,4-benzothiadiazine-3-acetic acid (14.4 g), 1-hydroxybenzotriazole (6.8 g) and 1-(3-dimethylaminopropyl)-3-ethylcarbodiimide, hydrochloride (9.6 g) at 0°–5°. Warm the reaction mixture to room temperature and stir for 18 hours. Concentrate the reaction mixture in vacuo, add dichloromethane and concentrate in vacuo. Dissolve the residue in ethyl acetate and extract with 1N sodium bicarbonate. Dry (MgSO$_4$) and concentrate the ethyl acetate solution in vacuo. Chromatograph the residue on silica gel using the Waters Prep 500 using ethylacetate as eluant to give N-[1(S)-ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanine, t-butyl ester.

C. Treat the product (11.0 g) prepared in Example 8B with dioxane saturated with hydrogen chloride (100 ml) for 20 hours at RT. Concentrate the reaction mixture in vacuo and tritrate the residue with anhydrous ether to isolate N-[1(S)-ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanine hydrochloride salt.

D. Treat the product of part C as described in Preparation 2I, C to obtain {1-N-[1(S)-[ethoxycarbonyl-2-4-(6-chloro-3,4,-dihydro-1,1-dioxo-7-sulfamoyl-1,2,4-benzothiadiazine-3-acetamido)phenyl]ethyl]-(S)-alanyl} cis,syn-octahydro-1H-indole-2(S)-carboxylic acid, benzyl ester.

E. Treat the product (7.3 g) of part D with 20% HBr in glacial acetic acid (30 ml) at 0°–5° and then stir at room temperature for 3 hr. Concentrate the reaction mixture in vacuo and wash the residue with ether to give the title compound, hydrobromide.

F. Treat the product (3.0 g) of part E with BioRad Resin (AG 50W-X2, 100–200 mesh) in water and then add to a column of the same resin. Elute with water, then water:pyridine 96:4 and then water:pyridine:absolute ethanol 76:20:4. Concentrate the fractions (iodine positive) in vacuo to give the title compound.

EXAMPLE 9

1-{N-[1(S)-Carboxy-2-[4-(6-chloro-3,4-dihydro-1,1-dioxo-7-sulfamoyl-1,2,4-benzothiadiazine-3-acetamido)phenyl]ethyl]-(S)-alanyl}cis,syn-octahydro-1H-indole-2(S)-carboxylic acid To the product from Example 8 (3.0 g) add 1N NaOH (20 ml) and treat as described in Example 2 to give the title compound.

EXAMPLE 10

1-{N-[1(S)-Ethoxycarbonyl-3-[4-(6-chloro-3,4-dihydro-1,1-dioxo-7-sulfamoyl-1,2,4-benzothiadiazine-3-acetamido)phenyl]propyl]-(S)-alanyl}-cis,syn-octahydro-1H-indole-2(S)-carboxylic acid Treat the product of Preparation 3IE as described in Example 8 to produce the title compound.

EXAMPLE 11

1-{N-[1(S)-Carboxy-3-[4-(6-chloro-3,4-dihydro-1,1-dioxo-7-sulfamoyl-1,2,4-benzothiadiazine-3-acetamido)phenyl]propyl]-(S)-alanyl}cis,syn-octahydro-1H-indole-2(S)-carboxylic acid Treat the product of Example 10 as described in Example 5 to produce the title compound.

By following the procedures described in the above preparations and examples, and by using the appropriate reagents, the following compounds may be prepared:

1-{Nα-[1(S)-ethoxycarbonyl-3-[4-(6-chloro-3,4-dihydro-1,1-dioxo-7-sulfamoyl-1,2,4-benzothiadiazine-3-acetamido)phenyl]propyl]-(S)-lysyl]-cis,syn-octahydro-1H-indole-2(S)-carboxylic acid;

1-{N-[1(S)-methoxycarbonyl-4-[4-(6-chloro-3,4-dihydro-1,1-dioxo-7-sulfamoyl-1,2,4-benzothiadiazine-3-acetamido)phenyl]butyl]-(S)-alanyl]-cis,syn-octahydro-1H-indole-2(S)-carboxylic acid;

2-{N-[1(S)-ethoxycarbonyl-3-[4-(6-chloro-3,4-dihydro-1,1-dioxo-7-sulfamoyl-1,2,4-benzothiadiazine-3-acetamido)phenyl]propyl]-(S)-alanyl]-1,2,3,4-tetrahydroisoquinoline-3(S)-carboxylic acid;

1-{N-[1(S)-(2-phenoxyethoxycarbonyl)-3-[4-(4-chloro-3-sulfamoylbenzamido)phenyl[propyl[-(S)-alanyl}-cis,syn-octahydro-1H-indole-2(S)-carboxylic acid;

1-{N-[1(S)-pivaloyloxymethoxycarbonyl)-3-[4-(4-chloro-3-sulfamoylbenzenesulfonamido)phenyl]-propyl]-(S)-alanyl}-cis,syn-octahydro-1H-indole-2(S)-carboxylic acid;

1-{N-[1(S)-ethoxycarbonyl-3-[4-(6-chloro-3,4-dihydro-1,1-dioxo-2-methyl-7-methylsulfamoyl-1,2,4-benzothiadiazine-3-acetamido)phenyl]propyl]-(S)-alanyl}-cis,syn-octahydro-1H-indole-2(S)-carboxylic acid;

1-{N-[1(S)-ethoxycarbonyl-3-[4-(4-chloro-3-sulfamoylbenzenesulfonamido)phenyl]propyl]-(S)-alanyl}-(S)-proline;

1-{N-[1(S)-carboxy-3-[4-(6-chloro-3,4-dihydro-1,1-dioxo-7-sulfamoyl-1,2,4-benzothiadiazine-3-acetamido)phenyl]propyl]-(S)-alanyl}-(S)-proline;

7-{N-[1(S)-carboxy-3-[4-(6-chloro-3,4-dihydro-1,1-dioxo-7-sulfamoyl-1,2,4-benzothiadiazine-3-acetamido)phenyl]propyl]-(S)-alanyl}-1,4-dithia-7-azaspiro[4.4]nonane-8(S)-carboxylic acid;

7-{N-[1(S)-carboxy-3-[4-(4-chloro-3-sulfamoylbenzamido)phenyl]propyl]-(S)-alanyl}-1,4-dithia-7-azaspira[4.4]nonane-8(S)-carboxylic acid;

2-{N-[1(S)-carboxy-3-[4-(4-chloro-3-sulfamoylbenzenesulfonamido)phenyl]propyl]-(S)-alanyl}-1,2,3,4-tetrahydroisoquinoline-3(S)-carboxylic acid;

1{N-[1(S)-ethoxycarbonyl-4-[2-(6-trifluoromethyl-3,4-dihydro-1,1-dioxo-7-sulfamoyl-1,2,4-benzothiadiazinyl-3-acetamido)phenyl]propyl]-glycyl}-cis,syn-octahydro-1H-indole-2(S)-carboxylic acid;

1-{N-[1(S)-ethoxycarbonyl-2-[4-(6-chloro-3,4-dihydro-2-benzyl-1,1-dioxo-7-sulfamoyl-1,2,4-benzothiadiazine-3-acetamido)phenylthio]ethyl]-(S)-alanyl}-cis,syn-octahydro-1H-indole-2(S)-carboxylic acid;

1-{N-[1(S)-ethoxycarbonyl-2-[4-(6-chloro-3,4-dihydro-1,1-dioxo-7-sulfamoyl-1,2,4-benzothiadiazine-2-benzyl-3-acetamido)phenyl]methoxyethyl]-(S)-alanyl}-cis,syn-octahydro-1H-indole-2(S)-carboxylic acid; and 1-{N-[1(S)-ethoxycarbonyl-3-[4-(6-chloro-3,4-dihydro-1,1-dioxo-7-sulfamoyl-1,2,4-benzothiadiazin-3-yl)methylthiophenyl]propyl]-(S)-alanyl}-cis,syn-octahydro-1H-indole-2(S)-carboxylic acid.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

I claim:

1. A method of reducing intraocular pressure in a mammal which comprises topically administering to an eye of said mammal in need of such treatment a composition comprising an intraocular pressure reducing effective amount of a compound represented by formula I:

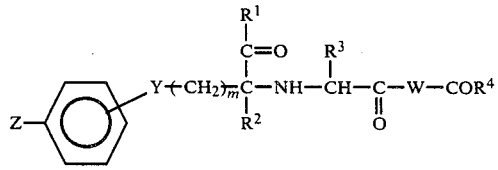

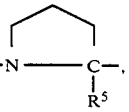

wherein W is

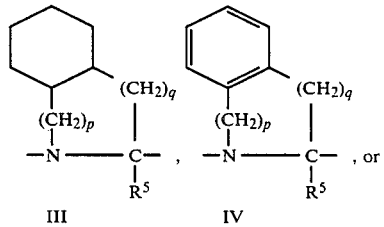

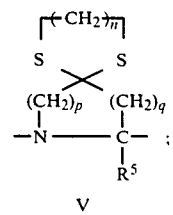

n is 0 or 1; m is 0 to 2;

p and q are each 0, 1 or 2, provided that the sum of p and q is 1 or 2, and that in formula V, p is not 0;

Y is —CH$_2$—, —CH$_2$O—, or —CH$_2$S—, attached at the 2 or 4 position of phenyl group;

Z is

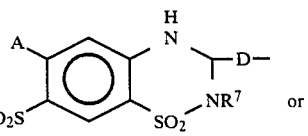

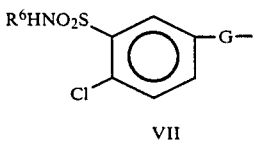

wherein
A is Cl or CF$_3$;

D is —(CH$_2$)$_u$— (wherein u is 1 or 2), —CH$_2$O—, —CH$_2$S—,

G is —CONR$^7$(CH$_2$)$_t$—, or —SO$_2$NR$^7$(CH$_2$)$_t$—; t is 0 or 1;

R$^1$ and R$^4$ are independently hydroxy, alkoxy having from 1 to 8 carbon atoms, K—X$_r$—(CH$_2$)$_s$—O—, wherein K is phenyl, substituted phenyl, 1- or 2-naphthyl, X is oxygen or sulfur, r is 0 or 1 and s is 0 to 4, (provided that when s is 0, r is 0) and wherein the substituents on the phenyl are chosen from group M, wherein M is halogen, hydroxy, trifluoromethyl, alkoxy having 1 to 6 carbon atoms, 2- and 3-furanyl, 2- and 3-thienyl, phenyl not substituted, phenyl substituted with halogen, hydroxy, trifluoromethyl, alkoxy having from 1 to 6 carbon atoms or alkyl having form 1 to 6 carbon atoms, —OCH₂OCO—alkyl wherein the alkyl has from 3 to 8 carbon atoms, —OCH₂CO—phenyl, wherein the phenyl substituted with group M, 1-glyceryl,

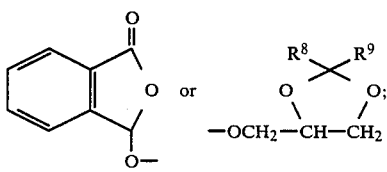

$R^2$, $R^5$, $R^6$ and $R^9$ are hydrogen or lower alkyl;
$R^3$ is hydrogen, lower alkyl or amino lower alkyl;
$R^7$ is hydrogen, lower alkyl or phenyl(lower)alkyl and
$R^8$ is hydrogen, lower alkyl, phenyl, or phenyl substituted by group M;
or a pharmaceutically acceptable salt thereof.

2. A method according to claim 1 wherein W is represented by formula III, IV or V.

3. A method according to claim 1 wherein W is represented by formula III or V.

4. A method according to claim 1 wherein W is represented by formula III or IV, wherein p is 0 and q is 1.

5. A method according to claim 1 wherein W is represented by formula V, wherein p is 1, q is 1, and n is 0.

6. A method according to claim 1 wherein $R^2$ and $R^5$ are hydrogen.

7. A method according to claim 1 wherein $R^4$ is hydroxy.

8. A method according to claim 4 wherein $R^3$ is methyl or aminobutyl.

9. A method according to claim 5 wherein $R^3$ is methyl or aminobutyl.

10. A method according to claim 8 wherein Z is represented by formula VI.

11. A method according to claim 9 wherein Z is represented by formula VI.

12. A method according to claim 10 wherein A is chlorine, and $R^6$ and $R^7$ are hydrogen or methyl.

13. A method according to claim 11 wherein A is chlorine, $R^6$ and $R^7$ are hydrogen or methyl.

14. A method according to claim 8 wherein Z is represented by formula VII.

15. A method according to claim 9 wherein Z is represented by formula VII.

16. A method according to claim 14 wherein $R^6$ is hydrogen or methyl.

17. A method according to claim 15 wherein $R^6$ is hydrogen or methyl.

18. A method according to claim 1 wherein $R^1$ is hydroxy, ethoxy, methoxy, phenoxyethoxy, or pivaloyloxymethoxy.

19. A method according to claim 1 wherein the compound is 1-{N-[1(S)-ethoxycarbonyl-2-[4-(3-sulfamoyl-4-chlorobenzamido)-phenyl]ethyl]-(S)-alanyl}-cis,syn-octahydro-1H-indole-2(S)-carboxylic acid.

20. A method according to claim 1 wherein the compound is 1-{N-[1(S)-ethoxycarbonyl-2-[4-(4-chloro-3-N-methylsulfamoylbenzamido)phenyl]ethyl]-(S)-alanyl}-cis,syn-octahydro-1H-indole-2(S)-carboxylic acid.

21. A method according to claim 1 wherein the compound is 1-{N-[1(S)-carboxy-2-[4-(4-chloro-3-sulfamoylbenzamido)phenyl]ethyl]-(S)-alanyl}-cis,syn-octahydro-1H-indole-2(S)-carboxylic acid.

22. A method according to claim 1 wherein the compound is 1-{N-[1(S)-carboxy-2-[4-(4-chloro-3-N-methylsulfamoylbenzamido)phenyl]ethyl]-(S)-alanyl}-cis,syn-octahydro-1H-indole-2(S)-carboxylic acid.

23. A method according to claim 1 wherein the compound is 1-{N-[1(S)-ethoxycarbonyl-3-[4-(4-chloro-3-sulfamoylbenzamido)-phenyl]propyl]-(S)-alanyl}-cis,-syn-octahydro-1H-indole-2(S)-carboxylic acid.

24. A method according to claim 1 wherein the compound is 1-{N-[1-(S)-ethoxycarbonyl-3-[4-(4-chloro-3-N-methylsulfamoylbenzamido)phenyl]propyl]-(S)-alanyl}-cis,syn-octahydro-1H-indole-2(S)-carboxylic acid.

25. A method according to claim 1 wherein the compound is 1-{N-[1(S)-ethoxycarbonyl-3-[4-(6-chloro-3,4-dihydro-1,1-dioxo-7-sulfamoyl-2H-1,2,4-benzothiadiazine-3-acetamido)phenyl]propyl]-(S)-alanyl}-cis,syn-octahydro-1H-indole-2(S)-carboxylic acid.

26. A method according to claim 1, further comprising administering to the eye of said mammal a composition comprising an intraocular pressure reducing effective amount of a beta-adrenergic blocking agent.

27. A method according to claim 26 wherein the beta adreneric blocking agent and the compound of formula I are administered topically together in the same composition.

28. A method according to claim 27 wherein the beta adrenergic blocking agent is selected from atenolol, metoprolol, nadolol, pindolol, propranolol, timolol, labetalol, carteolol, bunolol, betaxolol or dilevalol or pharmaceutically acceptable salts and/or isomers thereof.

29. A method according to claim 27 wherein the beta adrenergic blocking agent is timolol.

30. A method according to claim 27 wherein the beta adrenergic blocking agent is bunolol.

31. A method according to claim 1 wherein an anti-inflammatory amount of an anti-inflammatory steroid is also administered to said mammal.

32. A method according to claim 31 wherein said anti-inflammatory steroid and the compound of formula I are administered topically together in the same composition.

33. A method according to claim 31 wherein the anti-flammatory steroid is selected from hydrocortisone, cortisone, prednisolone, prednisone, dexamethasone, methylprednisolone, triamicinolone, betamethasone, alclometasone, flunisolide, beclomothasone clorocortolone, diflorasone halcinonide, fluocinonide, flucinolone, desoximetasone, medrysone, parametasone, 9,21-dichloro-17-[(2-furanylcarbonyl)oxy]-11-hydroxy-16α-methyl-pregna-1,4-diene-3,20-dione, or fluorometholone, or pharmaceutically acceptable salts, esters and or mixtures thereof.

34. A topical ophthalmologically acceptable composition useful for reducing intraocular pressure which comprises an effective amount of a compound of formula I or a pharmaceutically and ophthalmologically acceptable salt thereof

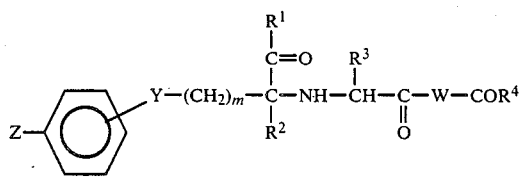

in combination with an ophthalmologically acceptable carrier for topical use, wherein
W is

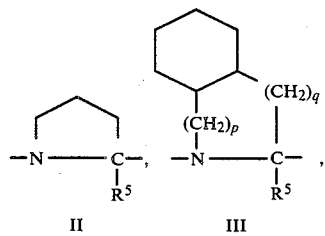

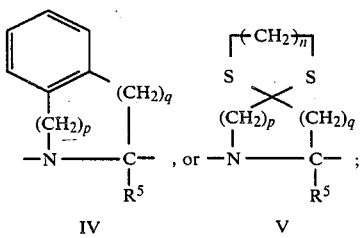

n is 0 or 1; m is 0 to 2;
p and q are each 0, 1 or 2, provided that the sum of p and q is 1 or 2, and that in formula V, p is not 0;
Y is —CH$_2$—, —CH$_2$O—, or —CH$_2$S—, attached at the 2 or 4 position of phenyl group;
Z is

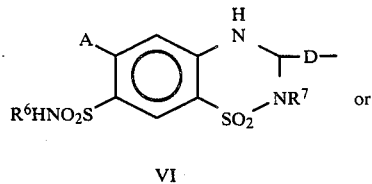

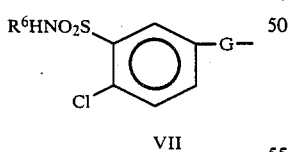

wherein
A is Cl or CF$_3$;
D is —(CH$_2$)$_u$— wherein u is 1 or 2, —CH$_2$O—, —CH$_2$S—, or

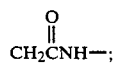

G is —CONR$^7$(CH$_2$)$_t$—, or —SO$_2$NR$^7$(CH$_2$)$_t$—; t is 0 or 1;
R$^1$ and R$^4$ are independently hydroxy, alkoxy having from 1 to 8 carbon atoms, K—X$_r$—(CH$_2$)$_s$—O—, wherein K is phenyl not substituted, substituted phenyl, 1- or 2-naphthyl, X is oxygen or sulfur, r is 0 or 1 and s is 0 to 4, provided that when s is 0, r is 0 and wherein the substituents on the phenyl are chosen from group M, wherein M is halogen, hydroxy, trifluoromethyl, alkoxy having 1 to 6 carbon atoms, 2- and 3-furanyl, 2- and 3-thienyl, phenyl not substituted, phenyl substituted with halogen, hydroxy, trifluoromethyl, alkoxy having from 1 to 6 carbon atoms or alkyl having from 1 to 6 carbon atoms, —OCH$_2$OCO—alkyl wherein the alkyl has from 3 to 8 carbon atoms, —OCH$_2$CO—phenyl, wherein the phenyl is substituted with group M, 1-glyceryl,

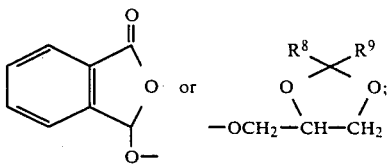

R$^2$, R$^5$, R$^6$ and R$^9$ are hydrogen or lower alkyl;
R$^3$ is hydrogen, lower alkyl or amino lower alkyl;
R$^7$ is hydrogen, lower alkyl or phenyl(lower)alkyl; and
R$^8$ is hydrogen, lower alkyl, phenyl, or phenyl substituted by group M; and
an effective amount of a beta adrenergic blocking agent such that the composition comprising the compound of formula I and the beta adrenergic blocking agent is effective to reduce intraocular pressure when administered to the eye of a mammal.

35. A composition according to claim 34 wherein the compound of formula I is
1-{N-[1(S)-ethoxycarbonyl-2-[4-(3-sulfamoyl-4-chlorobenzamido]-phenyl]ethyl]-(S)-alanyl}-cis,-syn-octahydro-1H-indole-2(S)-carboxylic acid;
1-{N-[1(S)-ethoxycarbonyl-2-[4-(4-chloro-3-N-methylsulfamoylbenzamido)phenyl]ethyl]-(S)-alanyl}-cis,syn-octahydro-1H-indole-2(S)-carboxylic acid;
1-{N-[1(S)-carboxy-2-[4-(4-chloro-3-sulfamoylbenzamido)phenyl]ethyl]-(S)-alanyl}-cis,syn-octahydro-1H-indole-2(S)-carboxylic acid;
1-{N-[1(S)-carboxy-2-[4-(4-chloro-3-N-methylsulfamoylbenzamido)phenyl]ethyl]-(S)-alanyl}-cis,-syn-octahydro-1H-indole-2(S)-carboxylic acid;
1-{N-[1(S)-ethoxycarbonyl-3-[4-(4-chloro-3-sulfamoylbenzamido)-phenyl]propyl]-(S)-alanyl}-cis,-syn-octahydro-1H-indole-2(S)-carboxylic acid;
1{N-[1(S)-ethoxycarbonyl-3-[4-(4-chloro-3-N-methylsulfamoylbenzamido)phenyl]propyl]-(S)-alanyl}-cis,syn-octahydro-1H-indole-2(S)-carboxylic acid; or
1-{N-[1(S)-ethoxycarbonyl-3-[4-(6-chloro-3,4-dihydro-1,1-dioxo-7-sulfamoyl-2H-1,2,4-benzothiadiazine-3-acetamido)phenyl]propyl]-(S)-alanyl}-cis,-syn-octahydro-1H-indole-2(S)-carboxylic acid.

36. The composition of claim 34 wherein the beta adrenergic blocking agent is atenolol, metoprolol, nadolol, pindolol, propranolol, timolol, labetalol, betaxolol, carteolol, bunolol or dilevatol, isomers thereof or their pharmaceutically acceptable salts.

37. The composition of claim 34 wherein said beta adrenergic blocking agent is timolol.

38. The composition of claim 34 wherein the beta adrenergic blocking agent is bunolol.

39. A topical ophthalmologically acceptable composition useful for reducing intraocular pressure which comprises an intraocular pressure reducing effective amount of a compound of formula I or a pharmaceutically and ophthalmologically acceptable salt thereof

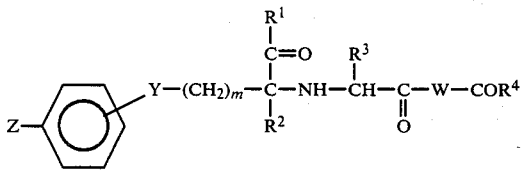

in combination with an opthalmologically acceptable carrier for topical use, wherein
W is

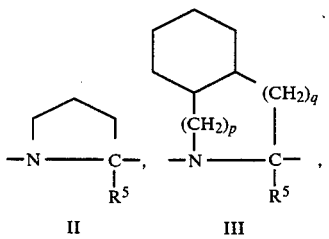

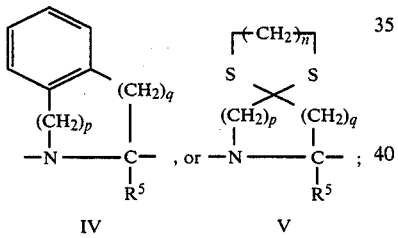

n is 0 or 1; m is 0 to 2;
p and q are each 0, 1 or 2, provided that the sum of p and q is 1 or 2, and that in formula V, p is not 0;
Y is —CH$_2$—, —CH$_2$O—, or —CH$_2$S—, attached at the 2 or 4 position of phenyl group;
Z is

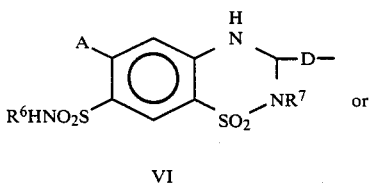

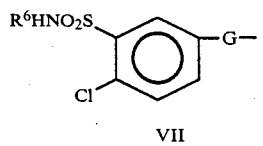

wherein
A is Cl or CF$_3$;

D is —(CH$_2$)$_u$—, wherein u is 1 or 2, —CH$_2$O—, —CH$_2$S—, or

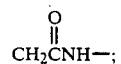

G is —CONR$^7$(CH$_2$)$_t$—, or —SO$_2$NR$^7$(CH$_2$)$_t$—; t is 0 or 1;
R$^1$ and R$^4$ are independently hydroxy, alkoxy having from 1 to 8 carbon atoms, K—X$_r$—(CH$_2$)$_s$—O—, wherein K is phenyl not substituted, substituted phenyl, 1- or 2-naphthyl, X is oxygen or sulfur, r is 0 or 1 and s is 0 to 4, provided that when s is 0, r is 0 and wherein the substituents on the phenyl are chosen from group M, wherein M is halogen, hydroxy, trifluoromethyl, alkoxy having 1 to 6 carbon atoms, 2- and 3-furanyl, 2- and 3-thienyl, phenyl not substituted, phenyl substituted with halogen, hydroxy, trifluoromethyl, alkoxy having from 1 to 6 carbon atoms or alkyl having from 1 to 6 carbon atoms, —OCH$_2$OCO—alkyl wherein the alkyl has from 3 to 8 carbon atoms, —OCH$_2$CO—phenyl, wherein the phenyl is substituted with group M, 1-glyceryl,

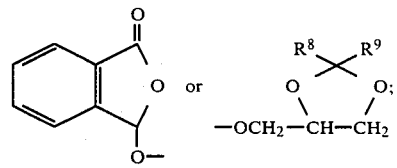

R$^2$, R$^5$, R$^6$ and R$^9$ are hydrogen or lower alkyl;
R$^3$ is hydrogen, lower alkyl or amino lower alkyl;
R$^7$ is hydrogen, lower alkyl or phenyl(lower)alkyl; and
R$^8$ is hydrogen, lower alkyl, phenyl, or phenyl substituted by group M; and
an amount of an anti-inflammatory steroid effective to reduce inflammation.

40. The composition of claim 39 wherein the compound of formula I is
1-{N-[1(S)-ethoxycarbonyl-2-[4-(3-sulfamoyl-4-chlorobenzamido)-phenyl]ethyl]-(S)-alanyl}-cis,-syn-octahydro-1H-indole-2(S)-carboxylic acid;
1-{N-[1(S)-ethoxycarbonyl-2-[4-(4-chloro-3-N-methylsulfamoylbenzamido)phenyl]ethyl]-(S)-alanyl}-cis,syn-octahydro-1H-indole-2(S)-carboxylic acid;
1-{N-[1(S)-carboxy-2-[4-(4-chloro-3-sulfamoylbenzamido)phenyl]ethyl]-(S)-alanyl}-cis,syn-octahydro-1H-indole-2(S)-carboxylic acid;
1-{N-[1(S)-carboxy-2-[4-(4-chloro-3-N-methylsulfamoylbenzamido)phenyl]ethyl]-(S)-alanyl}-cis,-syn-octahydro-1H-indole-2(S)-carboxylic acid;
1-{N-[1(S)-ethoxycarbonyl-3-[4-(4-chloro-3-sulfamoylbenzamido)-phenyl]propyl]-(S)-alanyl}-cis,-syn-octahydro-1H-indole-2(S)-carboxylic acid;
1-{N-[1(S)-ethoxycarbonyl-3-[4-(4-chloro-3-N-methylsulfamoylbenzamido)phenyl]propyl]-(S)-alanyl}-cis,syn-octahydro-1H-indole-2(S)-carboxylic acid; or
1-{N-[1(S)-ethoxycarbonyl-3-[4-(6-chloro-3,4-dihydro-1,1-dioxo-7-sulfamoyl-2H-1,2,4-benzothiadiazine-3-acetamido)phenyl]propyl]-(S)-alanyl}-cis,-syn-octahydro-1H-indole-2(S)-carboxylic acid.

41. The composition of claim 39 wherein the anti-inflammatory steroid is hydrocortisone, cortisone, prednisolone, prednisone, dexamethasone, methylprednisolone, tiramcinolone, betamethasone, fluorometholone, alclometasone, flunisolide, beclomethasone, clorocortolone, diflorasone, halcinonide, fluocinonide, flucinolone, desoximetasone, medrysone, parametahsone or 9,21-dichloro-17[(2-furanylcarbonyl)oxy]-11-hydroxy-16α-methyl-pregna-1,4-diene-3,20-dione, isomers and their pharmaceutically acceptable salts, esters, or mixtures thereof.

* * * * *